United States Patent [19]

Rusch et al.

[11] 4,261,726
[45] Apr. 14, 1981

[54] COMPOSITION FOR PLANT GROWTH REGULATION

[75] Inventors: Reinhard Rusch; Friedrich Arndt, both of Berlin, Fed. Rep. of Germany

[73] Assignee: Schering AG, Berlin and Bergkamen, Fed. Rep. of Germany

[21] Appl. No.: 15,281

[22] Filed: Feb. 26, 1979

Related U.S. Application Data

[63] Continuation of Ser. No. 842,365, Oct. 14, 1977, abandoned.

[30] Foreign Application Priority Data

Oct. 14, 1976 [DE] Fed. Rep. of Germany ....... 2646712

[51] Int. Cl.³ .................. A01N 43/02; A01N 59/00
[52] U.S. Cl. .......................................... 71/73; 71/65; 71/79; 71/82; 71/86; 71/87; 71/88; 71/89; 71/90; 71/91; 71/92; 71/94; 71/95; 71/96; 71/97; 71/100; 71/106; 71/111; 71/113; 71/114; 71/116; 71/117; 71/118; 71/121; 71/122
[58] Field of Search ...................... 71/73, 82, 90

[56] References Cited

U.S. PATENT DOCUMENTS

| | | | |
|---|---|---|---|
| 2,860,962 | 11/1958 | Bluestone | 71/73 |
| 3,152,879 | 10/1964 | Yale Jr. | 71/65 |
| 3,524,740 | 8/1970 | Young | 71/65 |
| 3,883,547 | 5/1975 | Schulz et al. | 546/209 |

FOREIGN PATENT DOCUMENTS 325957 2/1972 U.S.S.R. ..................................... 71/73

OTHER PUBLICATIONS

Schulz et al., "Composition containing 1,2,3-- etc.,"(1976) CA 86 No. 38598 q. (1977).

*Primary Examiner*—Glennon H. Hollrah
*Attorney, Agent, or Firm*—Michael J. Striker

[57] ABSTRACT

A composition for growth regulation of plants or for defoliating plants comprises in combination
(a) at least one compound of the formula $$\begin{array}{c} N\!=\!\!=\!\!C\!-\!H \\ \| \quad\quad | \\ N \quad C\!-\!N\!-\!CX\!-\!N \\ \diagdown_S\diagup \quad | \quad\quad \diagdown_{R_3} \\ \quad\quad R_1 \end{array} \begin{array}{c} R_2 \\ \diagup \\ \end{array}$$

wherein $R_1$ is hydrogen or alkyl of 1 to 3 carbon atoms and $R_2$ is hydrogen or alkyl of 1 to 4 carbon atoms and $R_3$ is alkyl of 1 to 4 carbon atoms, cycloalkyl of 5 to 8 carbon atoms, phenyl, halogenophenyl, methylphenyl, methoxyphenyl is nitrophenyl and X is oxygen or sulfur and (b) at least one other plant growth regulating or defoliating agent which, in combination with the compound at (a) results in a synergistic effect in regard to the growth regulating and defoliant properties. The composition is particularly suited for the defoliation of cotton plants.

12 Claims, No Drawings

COMPOSITION FOR PLANT GROWTH REGULATION

CROSS-REFERENCE TO RELATED APPLICATION

The present application is a continuation application of our copending patent application Ser. No. 842,365 filed Oct. 14, 1977 and now abandoned.

BACKGROUND OF THE INVENTION 1,2,3-thiadiazole-5-yl-urea derivatives are known as growth regulators for plants (German published application No. 2 234 816). These agents however do not have a sufficient activity in all cases.

Other growth regulating and/or defoliating agents are also known which in actual use do meet with the requirements of agricultural life.

It is therefore a object of the present invention to provide an agent for plant growth regulation which has a higher activity than the known regulators and defoliants.

SUMMARY OF THE INVENTION

This object is solved by a composition which in combination comprises

[a] at least one compound of the formula

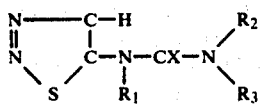

in which
$R_1$ is hydrogen or alkyl of 1 to 3 carbon atoms,
$R_2$ is hydrogen or alkyl of 1 to 4 carbon atoms,
$R_3$ is alkyl of 1 to 4 carbon atoms, cycloalkyl of 5 to 8 carbon atoms, phenyl, halogenophenyl, methylphenyl, methoxyphenyl or nitrophenyl and
X is oxygen or sulfur and

[b] at least one other plant growth regulating or defoliant agent which in combination with the compound at [a] results in a synergistic effect in regard to the growth regulating and defoliant properties when the compounds are present in amounts having a ratio of 100:1 to 1:1000 of the compound at [a] to the compound at [b].

The composition of the invention surprisingly has a growth regulating effect which is higher than the sum of the effects of the individual components above-identified at [a] and [b]. The composition is particularly suited for the defoliation of cotton plants which then have the optimum condition for applying cotton pickers for the harvesting of the balls.

Other plants can likewise be regulated as to their growth or can be defoliated such as for instance desired for the stocking or grasses, the lateral sprout formation of dicotyledons or for use for hibiscus or apple plants and other tree-forming plants.

DESCRIPTION OF THE INVENTION, ITS APPLICATION AND PREFERRED EMBODIMENTS

The preferred 1,2,3-thiadiazolyl-urea derivatives is 1-phenyl-3-(1,2,3-thiadiazole-5-yl).

The other components of the composition identified above at [b] may for instance be growth regulating and defoliating agents as follows:
auxin,
α-(2-chlorophenoxy)-propionic acid,
4-chlorophenoxyacetic acid,
2,4-dichlorophenoxyacetic acid,
indolyl-3-acetic acid,
indolyl-3-butyric acid,
α-naphthyl acetic acid,
β-naphthoxy acetic acid,
naphthylacetamide,
n-m-tolylphthalamido acid,
gibberellins,
S,S,S-tri-n-butyl-trithiophosphoric acid ester, cytokinine,
2-chloroethylphosphonic acid,
2-chloro-9-hydroxyfluorene-9-carboxylic acid,
2-chloroethyl-trimethylammoniumchloride,
N,N-dimethylaminosuccinic acid amide,
2-isopropyl-4-trimethylammonio-5-methylphenyl-piperidine-1-carboxylic acid esterchloride,
phenyl-isopropylcarbamate,
3-chlorophenyl-isopropylcarbamate,
ethyl-2-(3-chlorophenylcarbamoyloxy)-propionate,
maleic acid hydrazide,
2,3-dichloroisobutyric acid,
di-(methoxythiocarbonyl)disulfide,
1,1'-dimethyl-4,4'-bipyridylium-dichloride,
3,6-endoxohexahydrophthalic acid,
3-amino-1,2,4-triazole,
1,2,3-thiadiazolyl-5-yl-urea derivative,
1-(2-pyridyl)-3-(1,2,3-thiadiazole-5-yl)-urea
2-butylthio-benzthiazole,
2-(2-methylpropylthio)-benzthiazole,
3,4-dichloroisothiazole-5-carboxylic acid,
2,3-dihydro-5,6-dimethyl-1,4-dithiino-1,1,4,4-tetroxide,
arsenic acid,
cacodylic acid,
chlorates, preferably calcium chlorate, potassium chlorate, magnesium chlorate or sodium chlorate,
calcium cyanamide,
potassium iodide,
magnesium chloride,
abscisinic acid or nonanol.

Other thiadiazole-urea derivatives in addition to the above noted compound which can be used as the component [a] in the composition of the invention are for instance the following:

| Action compound | Physical Constants |
|---|---|
| 1-ethyl-1-phenyl-3-(1,2,3-thiadiazole-5-yl)-urea | m.p.: 200° C. (decomposed) |
| 1-(4-chlorophenyl)-3-(1,2,3-thiadiazole-5-yl)-urea | m.p.: 256° C. (decomposed) |
| 1-cyclohexyl-3-(1,2,3-thiadiazole 5-yl)-urea | m.p.: 215° C. (decomposed) |
| 1-(3-chlorophenyl)-3-(1,2,3-thiadiazole-5-yl)-urea | m.p.: 244° C. (decomposed) |
| 1-(4-methylphenyl)-3-(1,2,3-thiadiazole-5-yl)-urea | m.p.: 288° C. (decomposed) |
| 1-(3-methylphenyl)-3-(1,2,3-thiadiazole-5-yl)-urea | m.p.: 208° C. (decomposed) |
| 1-(3,4-dichlorophenyl)-3-(1,2,3-thiadiazole-5-yl)urea | m.p.: 236° C. (decomposed) |
| 1-methyl-3-(1,2,3-thiadizole-5-yl)-urea | m.p.: 174° C. |
| 1,1-dimethyl-3-(1,2,3-thiadiazole-5-yl)-urea | m.p.: 222° C. (decomposed) |

-continued

| Action compound | Physical Constants |
|---|---|
| 1,1-dimethyl-3-methyl-3-(1,2,3-thiadiazole-5-yl)-urea | m.p.: 129° C. |
| 1-methyl-3-methyl-3-(1,2,3-thiadiazole-5-yl)-urea | m.p.: 221° C. |
| 1-phenyl-3-(1,2,3-thiadiazole-5-yl)-thiourea | m.p.: 205° C. (decomposed) |
| 1-(4-chlorophenyl)-3-(1,2,3-thiadiazole-5-yl)-thiourea | m.p.: 213° C. (decomposed) |
| 1-methyl-1-phenyl-3-(1,2,3-thiadiazole-5-yl)urea | m.p.: 184° C. (decomposed) |
| 1-propyl-1-phenyl-3-(1,2,3-thiadiazole-5-yl)urea | m.p.: 190° C. (decomposed) |
| 1-butyl-1-phenyl-3-(1,2,3-thiadiazole-5-yl)-urea | m.p.: 198° C. (decomposed) |
| 1-(2-chlorophenyl)-3-(1,2,3-thiadiazole-5-yl)-urea | m.p.: 237° C. (decomposed) |
| 1-(2-methylphenyl)-3-(1,2,3-thiadiazole-5-yl)-urea | m.p.: 197° C. (decomposed) |
| 1-(2-nitrophenyl)-3-(1,2,3-thiadiazole-5-yl)-urea | m.p.: 229° C. (decomposed) |
| 1-(3-nitrophenyl)-3-(1,2,3-thiadiazole-5-yl)-urea | m.p.: 252° C. (decomposed) |
| 1-methyl-1-(2-methylphenyl)-3-(1,2,3-thiadiazole-5-yl)urea | m.p.: 215° C. (decomposed) |

The amounts to be employed of the composition are usually 1 to 10,000 g of total active agents per about 2.5 acres, preferably 10 to 1,000 g.

It will be understood that further active agents in addition to those above named may be added, for instance for defoliating, or plant protection purposes or as pesticides depending on the particular use.

The activity and speed of activity may be increased by the addition of certain additives such as organic solvents, wetting agents or oils. This may then permit a further reduction of the amount of active agents proper.

The composition of the invention is preferably used in the form of powders, dusting agents, solvents, emulsions or suspensions. In addition, liquid and/or solid carrier materials or diluents are included and, if desired, wetting agents, adhesion promoting agents, emulsifiers and/or dispersants may be added.

Suitable liquid carrier materials are, for instance, water, aliphatic and aromatic hydrocarbons, such as, benzene, toluene, xylene, xylene, cyclohexanone, isophorone, dimethylsulfoxide, dimethylformamide, and furthermore mineral oil fractions.

The solid carrier materials may be mineral earths, for instance tonsil, silicagel, talcum, kaolin, attaclay, limestone, silicic acid and plant products such as flours.

There may also be added surface active agents as for instance calcium lignosulfonate, polyoxyethylenealkylphenylether, naphthaline sulfonic acids and their salts, phenosulfonic acids and their salts, formaldehyde condensation products, fatty alcohol sulfates, as well as substituted benzene sulfonic acid and their salts.

The amount of total active agents in the compositions can be varied widely. The compositions may for instance include about 10 to 80% by weight of active agents, about 90 to 20% by weight of liquid or solid carrier materials and, if desired, up to 20% by weight of surface active agents.

The ratio of the 1,2,3-thiadiazole-urea derivatives of the present invention to other growth regulators or defoliants an average should be in the range of 100:1 up to 1:1,000 and preferably is between 10:1 and 1:100. The ratio depends on the sensitivity and strength of the plants, the time of application, the climatic conditions and conditions of the ground.

The application of the compounds can be effected in the customary manner, for instance when using water as carrier materials in spray amounts of about 100 to 1000 liter per about 2.5 acres. Use of the compositions in the so-called "low volume" or "ultra-low volume process" is likewise possible.

The specific 1,2,3-thiadiazole-urea derivatives of the invention are known compounds and can accordingly be made by known processes.

The following examples will further illustrate the invention.

EXAMPLES

Cotton plants were treated in a hothouse in the stage where they have 7 to 11 opened-up genuine deciduous leaves. The treatment was repeated four times.

In the following examples 30 and 31 the test was applied to young hibiscus plants.

The amounts of the composition of the invention used in the examples are stated in each example. The compositions were applied in 500 liters of water per about 2.5 acres.

Each active agent is assigned a Roman numeral to bring out the synergistic action of the compositions.

The effect was evaluated by determining 14 days after treatment the number of shed leaves. The results express the defoliation based on the number of deciduous leaves present prior to the treatment. In addition, in a separate column, the term E was calculated according to the method by S. R. Colby ("Calculating synergistic and antagonistic responses of herbicide combinations," Weeds 15/1 (1967), pages 20-22). This term E shows the additive effect of the individual components of the composition. Wherever a higher value was observed then the value for E, a truly synergistic effect, was present.

The term E was calculated according to the equation $$E = X + Y - \frac{XY}{100} \text{ or}$$

$$E = X + Y + Z - \frac{(XY + XZ + YZ)}{100} + \frac{XYZ}{10000}$$

In these equations the different symbols used having the following meaning:

X = percentage of defoliant action with a compound A at p kg of active agent per about 2.5 acres;
Y = percentage of defoliating agent with a compound B at q kg of active agent per about 2.5 acres;
Z = percentage of defoliating agent with a compound C at r kg of active agent per about 2.5 acres;
E = defoliating agent expected by use of A+B at p+q kg per about 2.5 acres and by use of A+B+C at p+q+r kg of about 2.5 acres, respectively.

EXAMPLE 1

Cotton (i.e. cotton) plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I  50 | 34.8 | |
| S,S,S-tri-n-butyl-trithio-phosphoric acid ester | = II  50 | 4.4 | |

| Compounds | Amounts of active agents in g/2.5 acres | defoliating action in % | E (Colby) |
|---|---|---|---|
| | I + II  50 + 50 | 43.5 | 37.7 |

EXAMPLE 2

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea S,S,S,-tri-n-butyl-trithio-phosphoric acid ester | = I  500 | 39.1 | |
| | = II  50 | 4.4 | |
| | I + II  500 + 50 | 56.5 | 41.1 |

EXAMPLE 3

Cotton wool plants were treated as above stated.

| Compounds | Amounts of active agents in g/2.5 acres | defoliating action in % | E (Colby) |
|---|---|---|---|
| 1-phenyl-1-(1,2,3-thiadiazole-5-yl)-urea sodium chlorate | = I  50 | 34.8 | |
| | = III  50 | 0 | |
| | I + III  50 + 50 | 54.4 | 34.8 |

EXAMPLE 4

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea sodium chlorate | = I  5 | 23.9 | |
| | = III  500 | 6.4 | |
| | I + III  5 + 500 | 34.8 | 28.8 |

EXAMPLE 5

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea 2,3-dihydro-5,6-dimethyl-1,4-dithiine-1,1,4,4-tetroxide | = I  5 | 21.7 | |
| | = IV  50 | 4.4 | |
| | I + IV  5 + 50 | 26.1 | 25.2 |

EXAMPLE 6

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea 2,3-dihydro-5,6-dimethyl-1,4-dithiine-1,1,4,4-tetroxide | = I  100 | 76.1 | |
| | = IV  100 | 19.6 | |
| | I + IV  50+50 | 78.3 | |

EXAMPLE 7

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea 1,1'-dimethyl-4,4'-bipyridylium-dichloride | = I  5 | 21.7 | |
| | = V  500 | 58.7 | |
| | I + V  5+500 | 78.7 | 67.7 |

EXAMPLE 8

Cotton wool plants were treated as above stated. This test was carried out under substantially less favorable light conditions than the preceding test in Example 7.

| Compounds | Amounts of active agents in g/2.5 acres | defoliating action in % | E (Colby) |
|---|---|---|---|
| 1-phenyl-3-(1,2,3-thiadiazole-5-yl)-urea 1,1'-dimethyl-4,4'-bipyridylium-dichloride | = I  5 | 3.6 | |
| | = V  50 | 26.8 | |
| | I + V  5 + 50 | 33.9 | 29.44 |

EXAMPLE 9

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea 1,1'-dimethyl-4,4'-bipyridylium-dichloride | = I  100 | 48.2 | |
| | = V  100 | 54.4 | |
| | I + V  50 + 50 | 59.6 | |

EXAMPLE 10

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea 3-amino-1,2,4-triazole | = I  50 | 72.1 | |
| | = VI  50 | 4.6 | |
| | I + VI  50 + 50 | 81.4 | 73.38 |

EXAMPLE 11

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)urea | = I | 50 | 72.1 |
| 3,6-endoxo-hexahydrophthalate, sodium | = VII | 5 | 4.6 |
| | I + VII  50 + 5 | 76.7 | 73.38 |

EXAMPLE 12

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I | 50 | 23.9 |
| magnesium chloride | = XI | 5 | 0 |
| | I + XI  50 + 5 | 34.8 | 23.9 |

EXAMPLE 13

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I | 50 | 80.4 |
| magnesium chloride | = XI | 50 | 4.4 |
| | I + XI  50 + 50 | 91.3 | 81.2 |

EXAMPLE 14

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I | 5 | 20.2 |
| potassium iodide | = VIII | 500 | 2.9 |
| | I + VIII  500 + 5 | 42.9 | 22.3 |

EXAMPLE 15

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I | 50 | 71.4 |
| potassium iodide | = VIII | 50 | 5.9 |
| | I + VIII  50 + 50 | 80.0 | 73.1 |

EXAMPLE 16

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I | 5 | 8.6 |
| 2-chloroethylphosphonic acid | = IX | 50 | 0 |
| | I + IX  5 + 50 | 21.2 | 8.6 |

EXAMPLE 17

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I | 50 | 68.6 |
| 2-chloroethylphosphonic acid | = IX | 5 | 0 |
| | I + IX  50 + 5 | 78.8 | 68.8 |

EXAMPLE 18

Cotton wool plants were treated as above stated.

| Compounds | Amounts of active agents in g/2.5 acres | defoliating action in % | E (Colby) |
|---|---|---|---|
| 1-phenyl-3-(-,2,3-thiadiazole-5-yl)-urea | = I | 50 | 71.4 |
| potassium iodide | = VIII | 50 | 5.9 |
| 2-chloroethylphosphonic acid | = IX | 5 | 0 |
| | I + VIII + IX  50+50+5 | 82.9 | 73.1 |

EXAMPLE 19

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I | 50 | 30.2 |
| gibberellinic acid A₃ | = X | 5 | 0 |
| | I + X  50 + 5 | 45.3 | 30.2 |

EXAMPLE 20

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I | 50 | 30.2 |
| gibberellinic acid A₃ | = X | 500 | 0 |
| | I + X  50 + 500 | 48.2 | 30.2 |

EXAMPLE 21

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)urea | = I     5 | 29.6 | |
| gibberellinic acid A₃ | = X     5 | 0 | |
| | I + X   5 + 5 | 37.0 | 29.6 |

EXAMPLE 22

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I     5 | 29.6 | |
| gibberellinic acid A₃ | = X     50 | 0 | |
| | I + X   5 + 50 | 48.2 | 29.6 |

EXAMPLE 23

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I     50 | 55.6 | |
| gibberellinic acid A₃ | = X     50 | 0 | |
| | I + X   50 + 50 | 77.8 | 55.6 |

EXAMPLE 24

Cotton wool plants were treated as above stated.

| Compounds | Amounts of active agents in g/2.5 acres | defoiating action in % | E (Colby) |
|---|---|---|---|
| 1-phenyl-3-(1,2,3-thiadiazole-5-yl)-urea | = I     5 | 8.5 | |
| 1-(2-pyridyl)-3-(1,2,3-thiadiazole-5-yl)-urea | = XII    50 | 36.2 | |
| | I + XII   5 + 50 | 48.9 | 41.6 |

EXAMPLE 25

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I     100 | 47.8 | |
| 1-(2-pyridyl)-3-(1,2,3-thiadiazole-5-yl)-urea | = XII    100 | 63.8 | |
| | I + XII   50 + 50 | 67.4 | |

EXAMPLE 26

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I     5 | 33.3 | |
| 2-butylthio-benzothiazole | = XIII   500 | 0 | |
| | I + XIII  5 + 500 | 66.7 | 33.3 |

EXAMPLE 27

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I     5 | 33.3 | |
| 2-(2-methylpropylthio)-benzothiazole | = XIV    500 | 0 | |
| | I + XIV   5 + 500 | 74.1 | 33.3 |

EXAMPLE 28

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I     5 | 33.3 | |
| 3,4-dichloroisothiazole-5-carboxylic acid | = XV    50 | 0 | |
| | I + XV   5 + 50 | 66.7 | 33.3 |

EXAMPLE 29

Cotton wool plants were treated as above stated.

| Compounds | Amounts of active agents in g/2.5 acres | defoliating action in % | E (Colby) |
|---|---|---|---|
| 1-phenyl-3-(1,2,3-thiadiazole-5-yl)-urea | = I     5 | 33.3 | |
| 3,4-dichloroisothiazole-5-carboxylic acid | = XV    500 | 0 | |
| | I + XV   5 + 500 | 74.1 | 33.3 |

EXAMPLE 30

In this test young hibiscus plants were treated.

| Compounds | Amounts of active agents in g/2.5 acres | defoliating action in % | E (Colby) |
|---|---|---|---|
| 1-phenyl-3-(1,2,3-thiadiazole-5-yl)-urea | = I     5 | 50.0 | |
| magnesium chlorate | = XVI    50 | 0 | |
| | I + XVI   5 + 50 | 63.6 | 50.0 |

EXAMPLE 31

In this test young hibiscus plants were treated.

| Compounds | Amounts of active agents in g/2.5 acres | | defoliating action in % | E (Colby) |
|---|---|---|---|---|
| 1-phenyl-3-(1,2,3-thiadiazole-5-yl)-thiourea | = XVII | 10 | 50.0 | |
| magnesium chlorate | = XVI | 1000 | 0 | |
| | XVII + XVI | 5 + 500 | 59.1 | |

EXAMPLE 32

Cotton wool plants were treated as above stated.

| Compounds | Amounts of active agents in g/2.5 acres | | defoliating action in % |
|---|---|---|---|
| 1-(2-methylphenyl)-3-(1,2,3-thiadiazole-5-yl)-urea | = XVIII | 100 | 65.5 |
| sodium chlorate | = III | 100 | 3.3 |
| | XVIII + III | 50 + 50 | 72.4 |

EXAMPLE 33

Cotton wool plants were treated as above stated.

| Compounds | Amounts of active agents in g/2.5 acres | | defoliating action in % | E (Colby) |
|---|---|---|---|---|
| 1-methyl-1-phenyl-3-(1,2,3-thiadiazole-5-yl)-urea | = XIX | 5 | 27.6 | |
| sodium chlorate | = III | 50 | 0 | |
| | XIX + III | 5 + 50 | 69.0 | 27.6 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A plant defoliant composition consisting essentially of as active ingredient
   (a) a compound of the formula

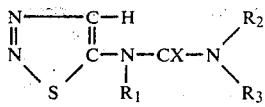

wherein $R_1$ is hydrogen or methyl, $R_2$ is hydrogen or $C_{1-4}$ alkyl, $R_3$ is methyl, cyclohexyl, phenyl, chlorophenyl, dichlorophenyl, methylphenyl or nitrophenyl, and X is oxygen or sulfur, and
   (b) a compound selected from the group consisting of calcium chlorate, magnesium chlorate, calcium cyanamide, potassium iodide, magnesium chloride, potassium chlorate, and sodium chlorate, said compounds (a) and (b) being present in amounts having a ratio (a):(b) of between 500:5 to 5:500, and being present in an amount sufficient to effect defoliation in admixture with a suitable inert carrier therefor.

2. A composition according to claim 1 wherein said compounds (a) and (b) are present in amounts having a ratio of (a):(b) of between 10:1 to 1:100.

3. A composition according to claim 1 wherein said compound (a) is 1-phenyl-3-(1,2,3-thiadiazole-5-yl)-urea.

4. A composition according to claim 1 wherein said compound (a) is 1-phenyl-3-(1,2,3-thiadiazole-5-yl)-urea and said compound (b) is potassium chlorate.

5. A composition according to claim 1 wherein said compound (a) is 1-phenyl-3-(1,2,3-thiadiazole-5-yl)-urea and said compound (b) is sodium chlorate.

6. A composition according to claim 1 wherein said composition contains 10 to 80% by weight of active ingredient and 90-20% by weight of carrier.

7. A composition according to claim 6 wherein said composition contains up to 20% by weight of a surface active agent.

8. A composition according to claim 1 wherein said carrier is a liquid.

9. A composition according to claim 1 wherein said carrier is a solid.

10. The method of defoliating plants which comprises applying to said plants an effective defoliating amount of a composition according to claim 1.

11. The method of defoliating leaves from plants which comprises applying to the foliage of said plants defoliating effective amount of a composition according to claim 1 in the form of its solution in water.

12. The method of claim 11 which comprises applying said composition in an amount 10 to 1000 g of active ingredient per 2.5 acres.

* * * * *